United States Patent

Yamkovoy (10) Patent No.: US 10,582,293 B2
(45) Date of Patent: Mar. 3, 2020

(54) WIND NOISE MITIGATION IN ACTIVE NOISE CANCELLING HEADPHONE SYSTEM AND METHOD

(71) Applicant: BOSE CORPORATION, Framingham, MA (US)

(72) Inventor: Paul Yamkovoy, Acton, MA (US)

(73) Assignee: Bose Corporation, Framingham, MA (US)

( * ) Notice: Subject to any disclaimer, the term of this patent is extended or adjusted under 35 U.S.C. 154(b) by 0 days.

(21) Appl. No.: 15/692,394

(22) Filed: Aug. 31, 2017

(65) Prior Publication Data
US 2019/0069074 A1   Feb. 28, 2019

(51) Int. Cl.
| | |
|---|---|
| G10L 21/0216 | (2013.01) |
| G10L 21/0208 | (2013.01) |
| G10K 11/178 | (2006.01) |
| H04R 1/10 | (2006.01) |
| H04R 5/033 | (2006.01) |
| G10K 11/00 | (2006.01) |
| A61F 11/14 | (2006.01) |

(52) U.S. Cl.
CPC ......... *H04R 1/1083* (2013.01); *G10K 11/002* (2013.01); *G10K 11/178* (2013.01); *G10K 11/17823* (2018.01); *G10K 11/17879* (2018.01); *H04R 5/033* (2013.01); *A61F 2011/145* (2013.01); *G10K 2210/1081* (2013.01); *H04R 2410/07* (2013.01); *H04R 2460/01* (2013.01)

(58) Field of Classification Search
CPC ........ H04R 3/02; H04R 1/1083; H04R 5/033; H04R 1/1041; G10K 11/17833; G10K 2210/1081; G10K 11/178; G10L 21/0216; G10L 21/0208

USPC ............................. 381/74, 93; 704/233, 226
See application file for complete search history.

(56) References Cited

U.S. PATENT DOCUMENTS

| | | | |
|---|---|---|---|
| 8,488,829 B2 | 7/2013 | Ring | |
| 8,620,650 B2 | 12/2013 | Walters et al. | |
| 2004/0167777 A1* | 8/2004 | Hetherington | G10L 21/0208 704/226 |
| 2012/0316872 A1* | 12/2012 | Stoltz | G10L 21/0216 704/233 |
| 2013/0148818 A1* | 6/2013 | Yamkovoy | H04R 1/1041 381/74 |
| 2013/0243214 A1 | 9/2013 | Penketh et al. | |

(Continued)

FOREIGN PATENT DOCUMENTS

| | | |
|---|---|---|
| EP | 3107312 A1 | 12/2016 |
| WO | 2006008492 A2 | 1/2006 |

OTHER PUBLICATIONS

International Search Report and Written Opinion dated Dec. 20, 2018 for Appl. No. PCT/US2018/048473.

*Primary Examiner* — Vivian C Chin
*Assistant Examiner* — Ubachukwu A Odunukwe
(74) *Attorney, Agent, or Firm* — Bose Corporation (57) ABSTRACT

Headphone systems and methods are provided to mitigate the impact of wind on active noise cancellation. At least one headphone system includes an earpiece with a speaker to convert a signal into acoustic energy in an acoustic volume. A microphone is acoustically coupled to an external environment and detects external noise. A control circuit is configured to detect wind and to adjust a feed-forward audio signal from the microphone based on the wind detection.

22 Claims, 7 Drawing Sheets

(56) References Cited

U.S. PATENT DOCUMENTS

| | | | |
|---|---|---|---|
| 2014/0072134 A1 | 3/2014 | Po et al. | |
| 2014/0185828 A1* | 7/2014 | Helbling | H03G 5/165 381/103 |
| 2014/0314245 A1* | 10/2014 | Asada | H04R 1/1083 381/71.6 |
| 2015/0104031 A1 | 4/2015 | Park et al. | |
| 2017/0133000 A1 | 5/2017 | Hendrix et al. | |
| 2018/0018954 A1* | 1/2018 | Liu | G10K 11/178 |

\* cited by examiner

WIND NOISE MITIGATION IN ACTIVE NOISE CANCELLING HEADPHONE SYSTEM AND METHOD

TECHNICAL FIELD

Aspects and implementations of the present disclosure are directed generally to audio systems, and in some examples, more specifically to systems and methods for Active Noise Reduction (ANR) in headphone systems.

BACKGROUND

Active Noise Reduction (ANR) headphones typically block undesired noise from a listener's ear by generating noise cancelling signals that destructively interfere with the undesired noise. Often the ANR headphones will include one or more microphones that measure the undesired noise. Based on the characteristics of the measured noise, the headphones will generate appropriate noise cancelling signals. The noise cancelling signals, once generated, are radiated by the headphones to reduce the undesired noise in the ear canal of the listener. In many instances, ANR headphones provide an improved listening experience when compared to traditional audio headphones.

SUMMARY

According to various aspects and examples discussed herein, there is provided a headphone system that adjusts Active Noise Reduction (ANR) operations based on detected wind conditions external to the headphone system. For example, wind may be detected by spectral analysis of an external audio signal, by a DC signal component (such as caused by constant mechanical pressure on an acoustic transducer, e.g., by wind), by comparison of external noise levels between a right and left side, or by other means, and a control circuit may adjust a feedback and/or feed-forward filter associated with the ANR circuitry of the headphone system when wind is detected. The feedback and/or feed-forward adjustment(s) may also vary based upon an amount, or level, of wind detected.

According to one aspect, a headphone system is provided that includes an earpiece configured to define an acoustic volume, a speaker to provide acoustic energy to the acoustic volume based on a received driver signal, a feed-forward microphone acoustically coupled to an external environment to detect at least external noise and generate a feed-forward audio signal, and a control circuit including an interface to receive a wind signal and configured to detect wind based at least in part upon the wind signal, the control circuit also configured to adjust the feed-forward audio signal based on the wind detection.

Certain examples also include a feedback microphone to detect at least residual noise within the acoustic volume, and generate a feedback audio signal, and wherein the control circuit is further configured to adjust the feedback audio signal based on the wind detection. The control circuit may adjust the feedback audio signal by adjusting one or more feedback filter coefficients applied to the feedback audio signal based on the wind detection. Some examples include a data store comprising a plurality of feedback filter coefficient sets, the control circuit being configured to select a first feedback filter coefficient set from among the plurality of feedback filter coefficient sets based on the wind detection.

In some examples, the control circuit is configured to adjust the feed-forward audio signal by adjusting one or more feed-forward filter coefficients applied to the feed-forward audio signal based on the wind detection. Further examples may include a data store comprising a plurality of feed-forward filter coefficient sets, the control circuit being configured to select a first feed-forward filter coefficient set from among the plurality of feed-forward filter coefficient sets based on the wind detection.

In certain examples, the interface is configured to receive the feed-forward audio signal as the wind signal, and the control circuit is configured to detect wind based at least in part on the feed-forward audio signal. The control circuit may analyze a spectral content of the feed-forward audio signal and to detect wind based at least in part on the spectral content.

According to certain examples, the feed-forward microphone may be a first feed-forward microphone to generate a first feed-forward audio signal and the headphone system further comprises a second feed-forward microphone to generate a second feed-forward audio signal, and the control circuit is configured to detect wind based at least in part on a comparison of the first feed-forward audio signal and the second feed-forward audio signal.

In some examples, the control circuit is further configured to detect a plurality of wind levels based at least upon the wind signal, and to adjust the feed-forward audio signal based at least in part on the detected wind level.

In certain examples, the control circuit is configured to adjust the feed-forward audio signal by disabling the feed-forward audio signal. In some examples, the control circuit is configured to disable the feed-forward audio signal by removing a microphone bias signal from the feed-forward microphone and/or the control circuit is configured to disable the feed-forward audio signal by applying a filter of zero gain to the feed-forward audio signal.

According to another aspect, another headphone system is provided that includes an earpiece configured to define an acoustic volume, a speaker to provide acoustic energy to the acoustic volume based on a received driver signal, a feedback microphone to detect at least residual noise within the acoustic volume and generate a feedback audio signal, a feed-forward microphone to detect at least external noise and generate a feed-forward audio signal, and a control circuit including an interface to receive the feed-forward audio signal and configured to detect wind based at least in part upon the feed-forward audio signal, the control circuit also configured to adjust the feed-forward audio signal based on the wind detection.

In some examples, the control circuit is configured to adjust a transfer function of a feed-forward filter applied to the feed-forward audio signal based on the wind detection. Certain examples include a data store comprising a plurality of feed-forward filter coefficient sets, the control circuit being configured to select a first feed-forward filter coefficient set from among the plurality of feed-forward filter coefficient sets based on the wind detection.

In some examples, the control circuit is further configured to adjust a transfer function of a feedback filter applied to the feedback audio signal based on the wind detection. Certain examples include a data store comprising a plurality of feedback filter coefficient sets, the control circuit being configured to select a first feedback filter coefficient set from among the plurality of feedback filter coefficient sets based on the wind detection.

According to certain examples, the feed-forward microphone is a first feed-forward microphone to generate a first feed-forward audio signal and the headphone system further comprises a second feed-forward microphone to generate a second feed-forward audio signal, and the control circuit is configured to detect wind based at least in part on a comparison of the first feed-forward audio signal and the second feed-forward audio signal.

According to yet another aspect, a method for operating a headphone system is provided. The method includes providing acoustic energy from a speaker of a headphone system to an acoustic volume based on a driver signal received at the speaker, detecting noise external to the acoustic volume using a feed-forward microphone, detecting wind by analyzing the noise external to the acoustic volume, generating a feed-forward audio signal at least partially indicative of the noise, and adjusting the feed-forward audio signal based at least in part on the wind detection.

In certain examples, the method further includes detecting residual noise within the acoustic volume, generating a feedback audio signal at least partially indicative of the residual noise, and adjusting the feedback audio signal based at least in part on the wind detection. Some examples adjust a transfer function of a feedback filter applied to the feedback audio signal based on the wind detection. In certain examples, the transfer function of the feedback filter is adjusted by selecting a filter coefficient set from among a plurality of filter coefficient sets based on the wind detection, and applying the selected filter coefficient set to the feedback filter.

Some examples include adjusting a transfer function of a feed-forward filter applied to the feed-forward audio signal based on the wind detection. The transfer function of the feed-forward filter may be adjusted in some examples by selecting a filter coefficient set from among a plurality of filter coefficient sets based on the wind detection, and applying the selected filter coefficient set to the feed-forward filter.

In certain examples, adjusting the feed-forward audio signal comprises disabling the feed-forward audio signal. In some examples, the feed-forward audio signal may be disabled by removing a microphone bias signal from the feed-forward microphone and/or by applying a filter of zero gain to the feed-forward audio signal.

Still other aspects, examples, and advantages of these exemplary aspects and examples are discussed in detail below. Examples disclosed herein may be combined with other examples in any manner consistent with at least one of the principles disclosed herein, and references to "an example," "some examples," "an alternate example," "various examples," "one example" or the like are not necessarily mutually exclusive and are intended to indicate that a particular feature, structure, or characteristic described may be included in at least one example. The appearances of such terms herein are not necessarily all referring to the same example. Various aspects and examples described herein may include means for performing any of the described methods or functions.

BRIEF DESCRIPTION OF THE DRAWINGS

Various aspects of at least one example are discussed below with reference to the accompanying figures, which are not intended to be drawn to scale. The figures are included to provide illustration and a further understanding of the various aspects and examples, and are incorporated in and constitute a part of this specification, but are not intended as a definition of the limits of the disclosure. In the figures, each identical or nearly identical component that is illustrated in various figures is represented by a like numeral. For purposes of clarity, not every component may be labeled in every figure. In the figures.

DETAILED DESCRIPTION

Various aspects and examples discussed herein are directed to headphone systems and methods that adjust Active Noise Reduction (ANR) operations based on wind detection, or wind level detection, in the environment in which the headphone systems are operated.

As discussed above, ANR headphones typically mask undesired noise at a listener's ear by generating cancelling signals that destructively interfere with the undesired noise. Noise cancelling functionality is desirable in various types of headphone systems, such as those designed for consumer products and those designed for commercial applications. In many instances, it is desirable to incorporate ANR technology within an aviation headphone system. In particular, ANR functionality allows a pilot, co-pilot, or passenger to perceive important audio content that may otherwise be obscured or masked by external noise and/or residual noise within the system.

According to certain aspects, examples of the headphone system described herein may be designed for an aircraft platform. For instance, the headphone system may be designed for use in aircraft that fly at altitudes of up to 40,000 or 45,000 feet (approximately 12,190 to 13,710 meters) and may require more than one pilot. In some instances, pilots may use cockpit blowers, fans, or other airflow devices for cooling. Often such fans and devices may blow air directly at the pilot's head, and often at a mild angle so that the airflow impacts the pilot's head more on one side than the other. Such airflow, or wind, may interfere with ANR performance, and in particular may interfere with feed-forward noise reduction systems that include one or more exterior microphones associated with the headphone system. For example, wind arriving at an exterior feed-forward microphone may cause signal components to be generated by the microphone that are not associated with true acoustic signals exterior to the headphone system. Such signal components are not related to exterior acoustic (noise) signals, yet may impact a feed-forward compensating signal intended to compensate for the exterior acoustic noise. Accordingly, a feed-forward component of an ANR system may increase noise, rather than decrease noise, inside the headphone when the feed-forward microphone is impacted by airflow or wind.

According to certain aspects, examples of the headphone system described herein may be designed for other environments where wind or airflow may be likely to occur. One such example is for sporting events or other outdoor environments. An example headphone system may be in use on the sidelines of a professional sporting event where high winds are likely to occur. Users of such headphone systems may also be very active, moving around quickly and rotating their head from side to side, such that airflow or wind may sporadically and unpredictably impact feed-forward ANR components. As another example, many users run or jog with headphones, or ride motorized equipment with headphones, causing airflow or wind that may degrade ANR performance.

Aspects and examples of headphone systems and methods described herein include components to detect the presence of wind and to adjust ANR operating characteristics as a result. In some examples, a feed-forward signal path may be adjusted to change the amount of impact it has on noise reduction, e.g., to reduce negative impact of wind-based signal components in a feed-forward signal. In some examples, the feed-forward portions of an ANR system may be disabled, e.g., equivalent to reducing a feed-forward signal response to zero. In some examples, feedback portions of an ANR system may also be adjusted when the feed-forward portions are adjusted.

As such, various aspects and examples discussed herein are directed to a headphone system that includes one or more components to detect wind (or airflow). Such components may include sensors to monitor environmental conditions and/or a state of an aircraft, and may include components that contribute to other portions of such a system, such as a feed-forward microphone for an ANR system, which may also provide a signal indicative of the exterior of the headphone system and may be used to detect wind. In other examples, different sensors may be used to detect wind. Each sensor may be integrated within a headphone structure of the system, or may be located external to the headphone structure and may communicate with components of the headphone system via a sensor interface. For example, an aircraft system may provide an output to indicate whether the pilot's fan is turned on or not.

Wind detection components are used to determine the appropriate settings for ANR circuitry of the headphone system. That is, the headphone system may select one or more settings for the ANR circuitry to accommodate various levels of influence that the wind may have on ANR performance. Accordingly, one or more adjustments to the ANR circuitry may adapt to prevent an unstable condition in the ANR circuitry and/or to substantially mask residual noise and/or external noise that would render the audio content delivered by the headphone structure substantially inaudible. Accordingly, various aspects and examples provide improved noise cancellation functionality that is not currently available in ANR headphone systems.

It is to be appreciated that examples of the systems and methods discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Though the elements of several views of the drawings herein may be shown and described as discrete elements in a block diagram and may be referred to as "circuit" or "circuitry," unless otherwise indicated, the elements may be implemented as one of, or a combination of, analog circuitry, digital circuitry, or one or more microprocessors executing software instructions. For example, software instructions may include digital signal processing (DSP) instructions to be executed by a digital signal processor. Unless otherwise indicated, signal lines may be implemented as discrete analog or digital signal lines, as a single discrete digital signal line with appropriate signal processing to process separate streams of audio signals, or as elements of a wireless communication system.

Some of the processing operations discussed herein may be expressed in terms of generating, determining, adjusting, filtering, distinguishing, and/or controlling, to name a few. The equivalent of determining, adjusting, filtering, comparing, selecting, and/or controlling can be performed by either analog or digital signal processing techniques and are included within the scope of this disclosure. Unless otherwise indicated, audio signals may be encoded in either digital or analog form; conventional digital-to-analog or analog-to-digital converters may not be shown in the figures but are intended to be within the scope of this disclosure. Additionally, delivery of an audio signal to an acoustic transducer, driver, speaker, or the like, may include amplification or other processing of the audio signal even though amplification stages may not be shown in the figures. Accordingly, additional signal processing may generally be included in any of the systems and methods disclosed herein, though such additional signal processing may be omitted from the figures or descriptions.

Figure 1:
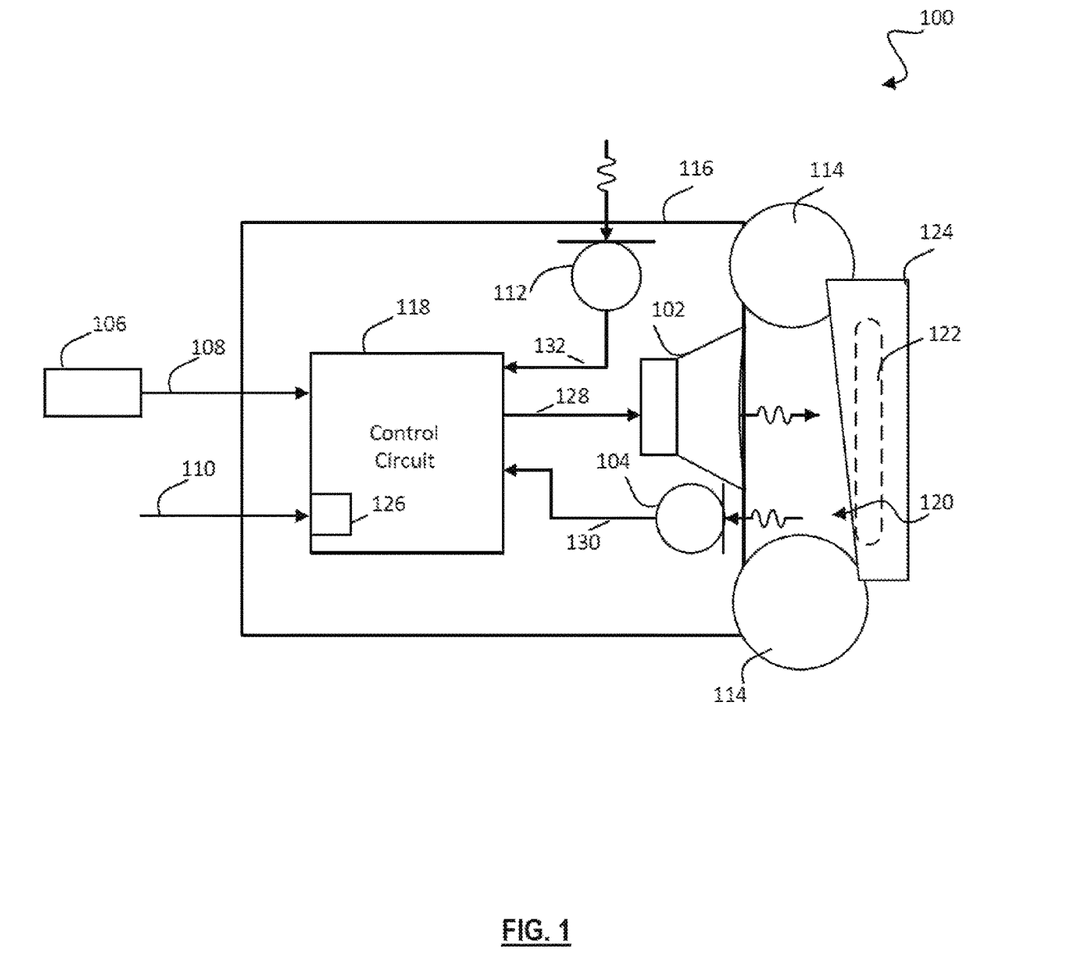
FIG. 1 is a block diagram of a headphone system according to various examples discussed herein.

Referring to FIG. 1, illustrated is a block diagram of a headphone system 100 according to examples discussed herein. As shown, the headphone system 100 includes at least one speaker 102, at least one microphone, such as the illustrated feedback microphone 104 and feed-forward microphone 112, one or more ear-cushions 114, an earpiece 116, and a control circuit 118. In response to receiving an input audio signal 108 from an audio source 106, the headphone system 100 is configured to generate and provide a driver signal 128 to the speaker 102. Once received at the speaker 102, the speaker 102 converts the driver signal to corresponding acoustic energy to deliver audio content to a listener positioned proximate the headphone system 100 (e.g., a user wearing the headphone system 100). In various examples, the speaker 102 delivers the acoustic energy to an acoustic volume that consists of an interior volume 120 of the earpiece 116 and a volume 122 within an ear 124 of the listener. As illustrated in FIG. 1, the earpiece 116 may be in contact with the ear 124 of the listener at the ear-cushions 114. However, in other examples, the ear-cushions 114 may be in contact with the head of the listener or within the pinna of the ear 124 of the listener. This may be the case in examples in which the headphone system 100 utilizes an in-ear earpiece or earbuds.

According to various examples, the structure of the headphone system 100, including the ear-cushions 114, may provide some degree of Passive Noise Reduction (PNR) by mechanically isolating the listener (e.g., the listener's ear 124) from external noise in the environment of the headphone system 100. As discussed herein, external noise may include any undesired acoustic energy that destructively interferes with the acoustic energy delivered to the listener. Within an aircraft environment, such noise may include cabin noise, aircraft noise, wind noise and/or weather noise, and/or speech content, to name a few examples.

In some examples the headphone system 100 may include an in-ear headphone structure where the ear-cushions 114 are positioned to create a seal on an inside of the listener's ear 124 and passively isolate the ear from the external noise. However, in certain other examples, the headphone system 100 may include an over-the-ear or an around-the-ear type headphone structure with the ear-cushions 114 positioned on an ear-cup and configured to sit on top of or enclose the ear 124 to isolate the ear 124 from external noise. While shown in FIG. 1 as including a single speaker, in various examples the speaker 102 may include a set of speakers (e.g., a speaker array) and one or both of the microphones 104 and 112 may include a set of microphones (e.g., a microphone array). Moreover, in certain examples the headphone system 100 may include a pair of speakers 102 (or speaker sets) and ear-cushion 114 sets; one for each ear of the listener. Various other examples of headphone arrangements, assemblies, and structures that provide some degree of PNR are discussed below with reference to FIG. 4 and FIG. 5.

In addition to the impact of PNR on the external noise, in various examples the headphone system 100 may use the feedback microphone 104 and/or the feed-forward microphone 112 to generate a driver signal that is adjusted to compensate for the external noise and/or residual noise. While shown in FIG. 1 as including both a feedback microphone 104 and a feed-forward microphone 112, it is appreciated that in certain examples the headphone system 100 may include just the feedback microphone 104 or just the feed-forward microphone 112. As illustrated, the feedback microphone 104 may be positioned proximate the ear 124 (e.g., proximate the ear canal) of the listener and may detect the acoustic energy delivered by the speaker 102 to the acoustic volume, as well as, residual external noise (e.g., noise that is not eliminated by the PNR described above or by feed-forward ANR techniques) within the acoustic volume. Based on the detected acoustic energy and residual noise, the feedback microphone 104 generates a feedback audio signal 130 that is communicated to the control circuit 118. As further discussed herein, the feedback microphone 104 may be used as a feedback loop with the control circuit 118 to monitor and adjust the driver signal 128 based on the detected acoustic energy and the residual noise. In particular, the control circuit 118 may apply a feedback filter to the feedback audio signal 130 to provide a feedback compensating signal that is combined with the input audio signal 108 to provide a driver signal 128 that compensates for the residual noise within the acoustic volume.

In various examples, the feed-forward microphone 112 also improves the ANR performance of the headphone system 100. As discussed, the feed-forward microphone 112 may be used in combination with the feedback microphone 104, or, in other examples, as an alternative to the feedback microphone 104. As illustrated in FIG. 1, the feed-forward microphone 112 may be positioned within the headphone system 100 to detect external noise from the environment of the headphone system 100. For instance, the feed-forward microphone 112 may be positioned on an exterior surface of the headphone system 100 or in another exposed position from which the feed-forward microphone 112 can detect the external noise before it reaches the ear 124 of the listener. Based on the detected external noise, the feed-forward microphone 112 may generate a feed-forward audio signal 132 that is communicated to the control circuit 118. While shown in FIG. 1 as a single control circuit 118, in various other examples each of the feedback microphone 104 and the feed-forward 112 microphone may have a dedicated control circuit 118. Each dedicated control circuit may be integrated within the corresponding microphone, integrated within the earpiece 116, or integrated within the control circuit 118.

As discussed, the feed-forward microphone 112 is positioned to detect the external noise before the noise is perceived by the listener. In various examples the feed-forward microphone 112 may be used as a feed-forward loop with the control circuit 118 to monitor and adjust the driver signal 128 based on the detected external noise. In particular, the control circuit 118 may apply a feed-forward filter to the feed-forward audio signal 132 to provide a feed-forward compensating signal that is combined with the input audio signal 108 to provide a driver signal 128 that compensates for the external noise.

As discussed, in certain examples each of the feedback microphone 104 and the feed-forward microphone 112 may be used in combination with the control circuit 118 to provide a feedback compensating signal and a feed-forward compensating signal that, when combined with the input audio signal 108, generate a driver signal 128 that compensates for effects that the external noise and/or the residual noise may have on the intelligibility of the audio content delivered to the listener. In one example, the control circuit 118 includes one or more feedback filters and one or more feed-forward filters. The feedback filters and feed-forward filters may be an analog filter or a digital filter implanted within ANR circuitry of the headphone system 100. For instance, the feedback filters and/or feed-forward filters may include linear and time-invariant filters. Each filter may be applied to the corresponding feedback audio signal 130 or feed-forward audio signal 132 to provide a compensating signal. For instance, the feedback filter may be applied by the control circuit 118 (e.g., ANR circuitry of the control circuit 118) to the feedback audio signal 130 to provide a feedback compensating signal, and the feed-forward filter may be applied by the control circuit 118 (e.g., ANR circuitry of the control circuit 118) to the feed-forward audio signal 132 to provide a feed-forward compensating signal.

To generate a driver signal 128 that is adjusted to compensate for the external noise and/or the residual noise, the control circuit 118 may combine the feedback compensating signal and/or the feed-forward compensating signal with the input audio signal 108. It is appreciated that a combination of the feedback compensating signal and the input audio signal 108 provides a driver signal 128 that is adjusted to compensate for the residual noise, and a combination of the feed-forward compensating signal and the input audio signal 108 provides a driver signal 128 that is adjusted to compensate for at least the external noise. Accordingly, an example of the headphone system 100 that includes both a feedback microphone 104 and a feed-forward microphone 112 offers the benefit of complete ANR. Each feedback filter and feed-forward filter may be described by a corresponding transfer function and filter coefficients that define the gain, phase, and frequency response of the feedback filter or the feed-forward filter. The performance of each feedback filter or feed-forward filter may be adjusted by changing the transfer function and/or the one or more filter coefficients associated with that feedback filter or feed-forward filter.

As discussed above, in some instances a windy environmental condition, or other airflow in the vicinity of the headphone system 100, such as a cooling fan or blower directed to a pilot's head, for instance, may have an impact on performance of active noise reduction, and in particular on feed-forward components that may generate non-acoustic feed-forward signal components because of the airflow. For example, airflow near the feed-forward microphone 112 may cause pressure variations unrelated to external acoustic noise and these pressure variations may be fed into the further ANR components, which may lead to undesirable operation or instability of the ANR functionality.

To accommodate windy conditions, the headphone system 100 may detect and/or quantify the presence of wind using a wind detector 126. The wind detector 126 may have an input to receive a wind signal 110 upon which the wind detector 126 may make a determination as to the presence and/or strength of wind or other airflow in the environment. In some examples, the wind signal 110 may be provided by the feed-forward microphone 112, and may be the feed-forward audio signal 132, or may be a signal derived from the feed-forward audio signal 132. In some examples, the wind signal 110 may come from another source or sensor, such as an additional microphone or pressure transducer that may be optimized to detect frequency or pressure components associated with wind. In some examples the wind signal 110 may be a user input through a user interface. Additional examples of the headphone system 100 may also include other types of environmental sensors from which the control circuit 118 may adjust the operation of ANR components.

Figure 2:
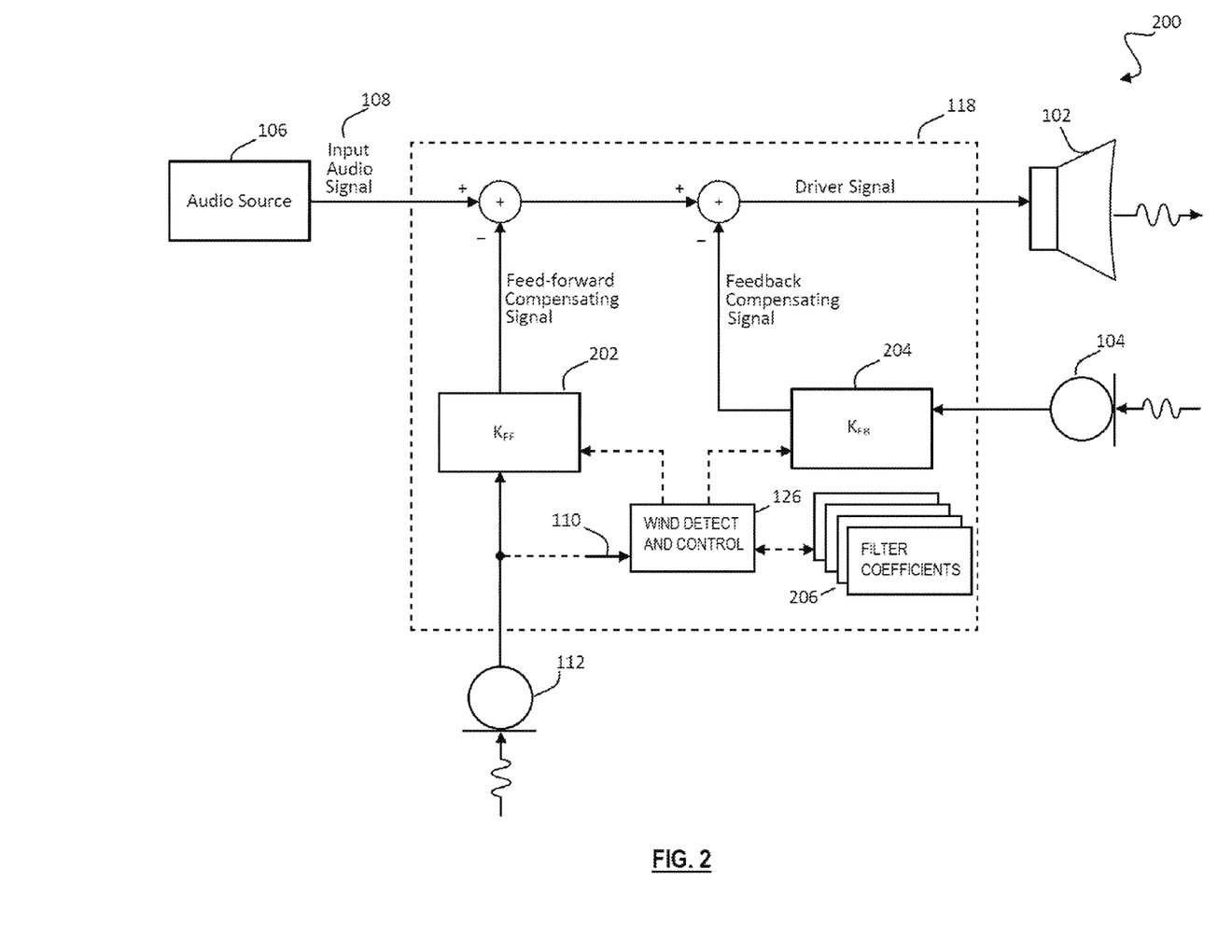
FIG. 2 is a block diagram showing adjustments to a feedback filter and a feed-forward filter based on wind detection, according to various examples discussed herein.

Based on wind detection by the wind detector 126, the control circuit 118 may make one or more adjustments to ANR circuitry (e.g., one or more feedback filters and/or feed-forward filters) to effect a change in the acoustic energy delivered to the listener. In particular, the control circuit 118 may adjust filter coefficients of one or more feed-forward filters and/or feedback filters to compensate or mitigate any deleterious effects of the wind on feed-forward and/or feedback components of ANR operations. Referring to FIG. 2, illustrated is a block diagram showing adjustments to a feed-forward filter 202 ("$K_{FF}$") and a feedback filter 204 ("$K_{FB}$") based on wind detection by a wind detector 126, according to various examples.

As illustrated in FIG. 2, an example headphone system 200 may adjust feed-forward and/or feedback noise reducing signal paths based on a detection of wind by the wind detector 126. For example, the control circuit 118 may adjust a transfer function and/or filter coefficient(s) of the feed-forward filter 202 and/or a transfer function and/or filter coefficient(s) of the feedback filter 204 to compensate for one or more effects of detected wind on ANR operations. The feed-forward filter 202 provides a feed-forward compensating signal, and the feedback filter 204 provides a feedback compensating signal, each of which may be subtracted from an input audio signal 108 (from an audio signal source 106) to provide a driver signal to the speaker 102.

For example, the wind detector 126 may detect wind and, in response, the control circuit 118 may disable the feed-forward portions of the ANR, for example, by zeroing out the transfer function ($K_{FF}$) of the feed-forward filter 202 (e.g., providing a filter with zero gain), or by disconnecting the feed-forward microphone 112 from the feed-forward filter 202, or by disconnecting the feed-forward compensating signal from the audio path between the audio source 106 and the speaker 102. The control circuit 118 may disconnect the feed-forward microphone 112 by removing a microphone bias signal from the feed-forward microphone 112. This may be done by applying a signal that removes the microphone bias gradually over a period of time, rather than instantaneously, to avoid generating any audible artifacts associated with the change. When the feed-forward portion of the ANR is disabled, it may be necessary to adjust the feedback signal path to compensate, at least partially, for the change. The control circuit 118 may load new filter coefficients, or alternate transfer function information, from a memory 206 that stores such filter coefficients or information, into the feedback filter 204. In some examples, when the feed-forward portion of the ANR is disabled, it may not be necessary to adjust the feedback signal path at all.

In some examples, the wind detector 126 may adjust the feed-forward operation, rather than disable the feed-forward portions of the ANR, by, e.g., loading new filter coefficients or a new transfer function into the feed-forward filter 202. Such a change to the feed-forward operation may make it beneficial to also change the operation of the feedback portions of the ANR, and the control circuit 118 may adjust or alter the filter coefficients and/or transfer function of the feedback filter 204, though, in some examples, the feedback signal path may remain unchanged. In some examples, the feed-forward filter and/or feedback filter adjustments may be made in accordance with a level of wind detected. For example, where the wind detector 126 detects lighter wind or airflow that causes less impact on the ANR components, the control circuit 118 may adjust the feed-forward filter and/or feedback filter in a less aggressive manner than where the wind detector 126 detects stronger wind or airflow that causes more impact on the ANR components.

While a memory 206 is shown in FIG. 2 for storage of filter coefficients and/or transfer function information, in some examples the control circuit 118 may adjust the transfer function of either filter 202, 204 by other means, such as by calculating new filter coefficients and/or transfer functions, or by sending commands to either of the filters 202, 204 to make adjustments in particular ways, such as by altering response in certain ways, such as at certain frequencies or frequency band(s) or by certain phase responses, etc.

In some examples, the control circuit 118 may adjust feed-forward or feedback operation in other manners, based upon the detection of wind presence, characteristic, or intensity. For example, instead of adjusting transfer functions and/or filter coefficient(s), the control circuit 118 may make other adjustments, e.g., directly to the feed-forward audio signal and/or feed-forward compensating signal, and/or directly to the feedback audio signal and/or feedback compensating signal, such as by band-limiting, attenuating, phase adjusting, or removal of such signals, or by disconnection or re-routing of signal paths between the various components, etc. Additionally, in some examples, the control circuit 118 may change other filter characteristics and/or filter types. In some examples, the control circuit 118 may alter a balance between left and right signal levels. In certain examples, the control circuit 118 may alter a blend, or relative impact, of feed-forward and feedback ANR components.

In some examples, the control circuit 118 may adjust feed-forward and/or feedback operation between two levels, e.g., whether there is or is not wind detected by the wind detector 126. In some examples, the control circuit 118 may adjust feed-forward and/or feedback operation across multiple levels, e.g., a first selected mode of operation when no wind is detected, a second selected mode of operation when light wind is detected, and a third selected mode of operation when heavy wind is detected. Each mode of operation may be defined by a combination of feed-forward and/or feedback signal path responses, e.g., filter coefficients or transfer functions of the feed-forward filter 202 and the feedback filter 204, for example. Additional modes of operation may be defined for additional levels or other characteristics of the wind or airflow detected in the environment.

Some examples of headphone systems in accord with those disclosed herein may include a left and right speaker 102, and accordingly may include feed-forward ANR components on each side and may also include feedback ANR components on each side. In some examples, one or more wind detectors 126 may detect wind on either the left side or the right side independently of each other. Alternately, one or more wind detectors 126 may process a wind signal 110 from a left side in parallel with processing a wind signal 110 from a right side, and may compare relative signal energies between the left and right sides to determine or detect the presence of wind. For example, background noise may have comparable levels on a right and left side of a headphone system, but wind may impact one side more than the other side. Accordingly, a sufficient discrepancy of signal energies from one side to the other may indicate the presence of wind on the "louder" side of the headphone system, and in some examples a wind detector 126 may measure such a discrepancy between signal energies to detect wind on one side or the other.

In some examples, the control circuit 118 makes one or more feed-forward and/or feedback signal path adjustments when a detected wind level exceeds one or more thresholds. In certain examples, the wind detector 126 may delay indicating wind, or the control circuit 118 may delay adjustments, until a consistent wind detection condition exists.

In various examples the control circuit 118 may be external to or may be integrated within an earpiece 116 of, e.g., system 100, 200. For instance, the control circuit 118 may be integrated within a headband or earpiece of a headphone system. In certain other examples, the control circuit 118, or portions thereof, may be implemented within an audio signal source (e.g., a mobile device) in communication with the headphone system.

FIGS. 3A-3E illustrate various examples of wind detectors 126 that may be suitable for headphone systems in accord with aspects and examples disclosed herein.

Figure 3A:
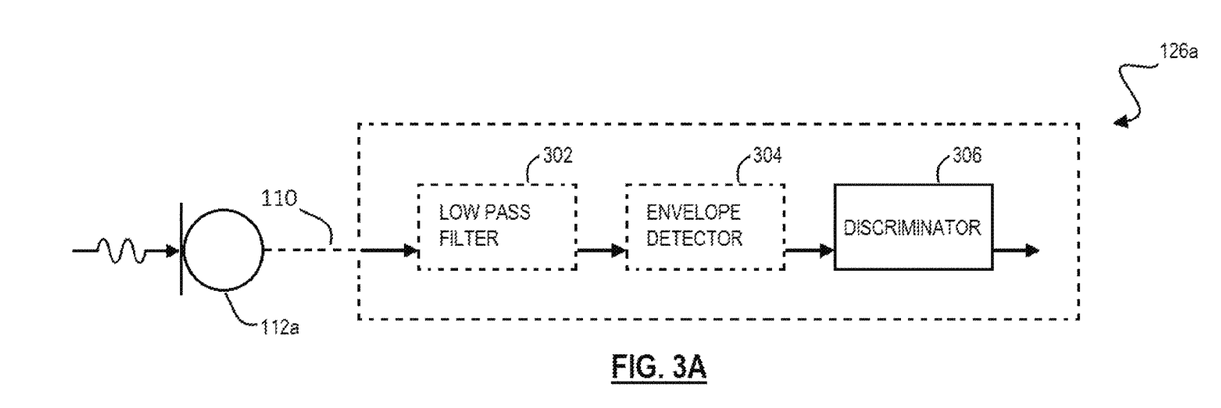
FIGS. 3A-3E are block diagrams of examples of wind detectors according to various examples discussed herein.

With reference to FIG. 3A, an example wind detector 126a is shown that detects low frequency components in a wind signal 110 to detect the presence of wind. Airflows such as wind tend to produce signals being heavily weighted toward lower frequency components, such as, for example below 30 Hz. Accordingly, detection of significant signal energy below, e.g., 30 Hz or less, may indicate the presence of wind. The wind signal 110 may be provided by a feed-forward microphone 112a, as shown, or may be provided by a different microphone or sensor, and may be provided by a sensor or microphone that provides some optimization for picking up such lower frequency components. The wind detector 126a may analyze or detect the presence of wind by analyzing the wind signal 110 for spectral content likely to be caused by wind, such as having significant signal energy below 30 Hz or less. The wind detector 126a may include a low pass filter 302 to filter out high frequency components above 30 Hz. In some examples, the low pass filter 302 may filter out components above about 25 Hz, or above about 20 Hz. The wind detector 126a may include an envelope detector 304 that detects a signal envelope, such as by smoothing or time-averaging an amplitude of the filtered wind signal, or otherwise detecting an amplitude or signal strength. A discriminator 306 compares the value(s) from the envelope detector 304 to one or more thresholds to detect wind and/or detect among various levels of wind. For example, a higher output from the envelope detector 304 indicates higher signal energies in the lower frequencies, which in turn may indicate higher wind conditions.

In some examples, the wind detector 126a may not include a low pass filter 302, such as may be the case if the wind signal 110 is provided by a sensor that limits or reduces higher frequency components before the wind signal 110 is provided to the wind detector 126a. Additionally, in some examples, the wind detector 126a may not include an envelope detector 304, such as may be the case if the wind signal 110 is provided by a suitable sensor that may indicate a measure of lower frequency content without the need for an envelope detector 304. Alternately, the discriminator 306 may incorporate functionality that compares signal amplitude or signal energy to threshold values without the necessity of an envelope detector 304.

Figure 3B:
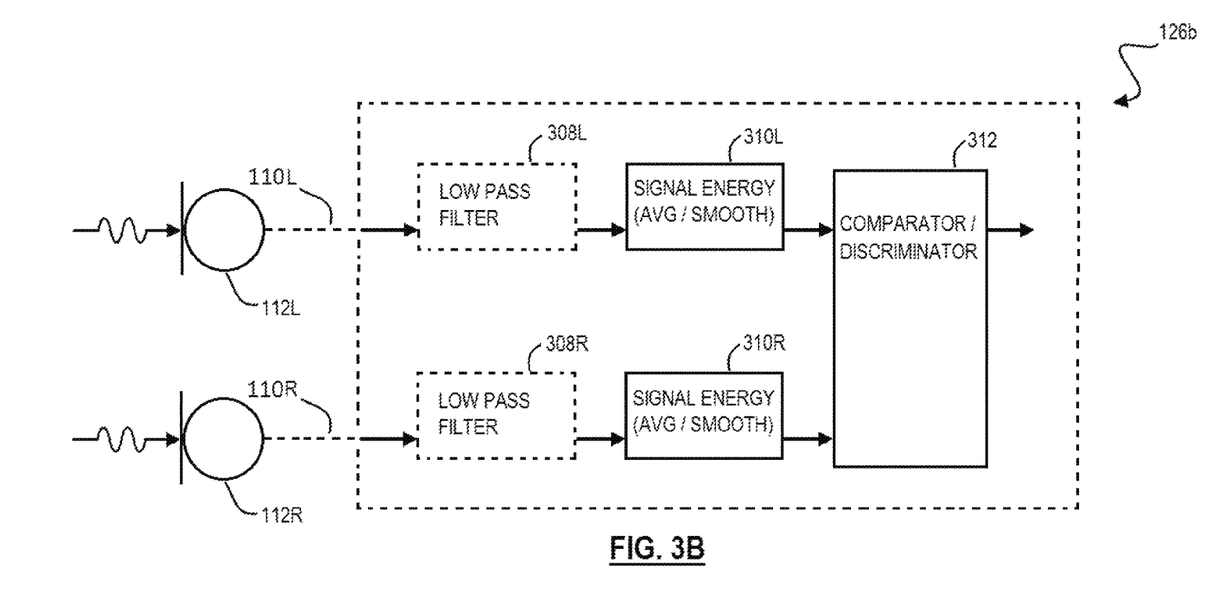

FIG. 3B illustrates an example wind detector 126b that analyzes wind signals 110 from a left and right side of various example headphone systems. As with the wind detector 126a, a left wind signal 110L and a right wind signal 110R may be filtered to remove higher frequency components by respective low pass filters 308L, 308R. Such may be the case when, as illustrated, the wind signals 110 are received as feed-forward audio signals provided by feed-forward microphones 112, having spectral content beyond the lower frequencies of interest. Respective signal energy measurement blocks 310L, 310R measure the left and right signal content and provide an indication of signal levels among the lower frequencies of interest. The signal energy measurement blocks 310 may include any of various components or methods to indicate signal levels, which may include smoothing, averaging, amplitude or power measurement, and/or envelope detection. A comparator or discriminator 312 measures or detects the difference in signal levels between the left and right sides, and may compare each signal level to one or more thresholds, and/or may compare the difference in signal levels to one or more thresholds, to detect wind and/or detect among various levels of wind, as discussed above. The wind detector 126b may also indicate which of the left or right sides, or both, is in a windy condition. In some examples the control circuit 118 may adjust ANR operation (as discussed above) only on one side when wind is detected only on one side, or the control circuit 118 may adjust the windy side differently than the control circuit 118 adjusts the other side.

Figure 3C:
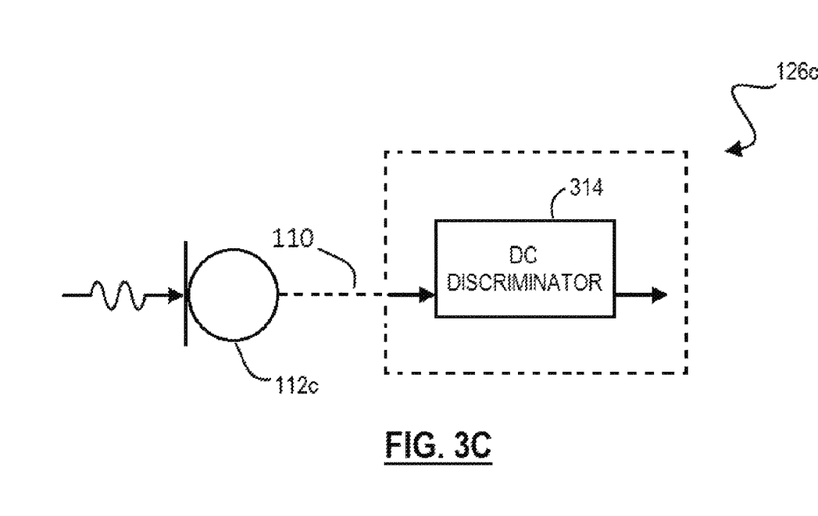

FIG. 3C illustrates an example wind detector 126c that analyzes the wind signal 110 for a direct current (DC) component. For example, airflow or wind on various microphones or other sensors may cause a DC bias to exist in their output signals. If such a signal is provided as the wind signal 110, a DC discriminator 314 may detect and/or compare the DC component to one or more thresholds to detect wind.

Figure 3D:
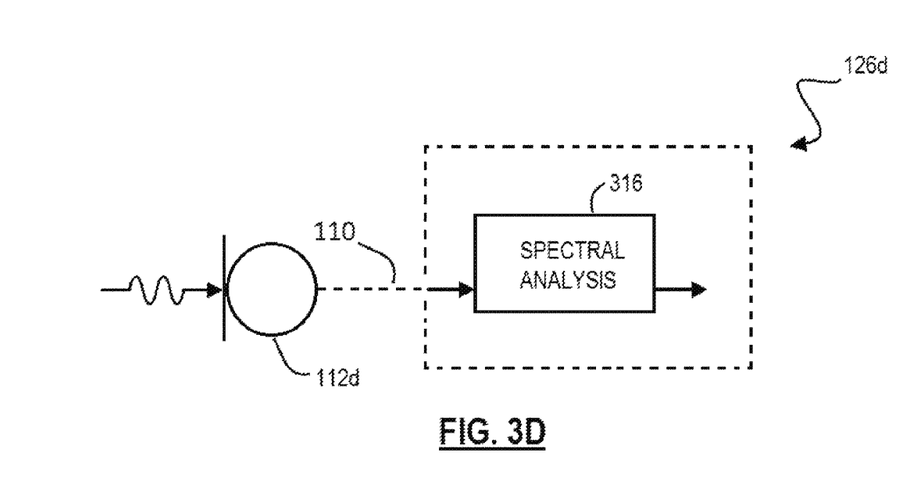

FIG. 3D illustrates an example wind detector 126d that includes a spectral analyzer 316 to analyze the wind signal 110 in various ways to determine the presence of wind. As discussed above, a signal from a feed-forward microphone 112d, as shown, may provide a signal having significant signal content at frequencies below 30 Hz, 25 Hz, 20 Hz, or lower, and a spectral analyzer can be used to look for more specific spectral content to indicate wind. Additionally, various examples may be designed for various expected environmental conditions having more or less predictable spectral signatures for the type of wind that may be expected. For example, cockpit blowers may generate spectral signatures that are identifiable and/or distinguishable from wind on a sporting event field, for instance, and in some examples the control circuit may make differing adjustments to the ANR components based upon characteristics of the wind detected. Additionally, in some examples, and as discussed above, the wind signal 110 may be provided by other types of sensors or microphones (rather than the feed-forward microphone 112d, as shown), and may be suitable for a certain spectral analysis by the spectral analyzer 316.

Figure 3E:
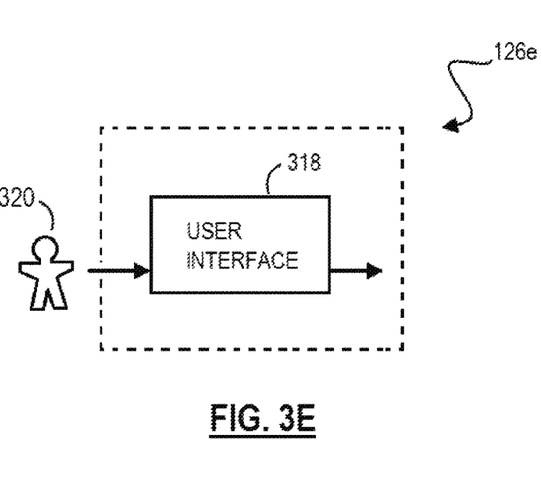

FIG. 3E illustrates an example wind detector 126e that provides a user interface to allow user selection of wind conditions and/or configuration of the ANR components to account for wind effects. For example, the user interface 318 may be a graphical user interface associated with the headphone system and/or may be associated with a mobile phone application or other control interface external to but in communication with the headphone system. In some examples, the user may be presented with options to select among various wind conditions, such as "wind" or "no wind," and in some examples options may include "light wind" or "heavy wind," or the like, and further in some examples options may include separate "left" and "right" wind indications, etc., to be selected by the user. In some examples, the user interface 318 may include one or more physical switches to indicate the presence or level of wind at one or more locations (e.g., left, right). In some examples, the user interface 318 may provide allowance for a voice command, which may or may not include a wake-up command, to indicate wind characteristics. In some examples, the user interface 318 may include a touch sensor. Other examples may include varying forms of user interface schemes.

While numerous examples of wind detectors 126 are illustrated in FIGS. 3A-3E, numerous variations exist from those illustrated and various alternate wind detectors 126 are contemplated. Any suitable method or arrangement may be used to measure, indicate, or detect wind and/or wind conditions in various examples of headphone systems described herein. For example, an example headphone system may include a resonant cavity, such as a Helmholtz resonator, to produce a mild "whistle" that may be detected by suitable signal analysis and/or processing. In some examples, a microphone or other sensor may exhibit non-linear characteristics in the presence of wind, e.g., due to flattening of a diaphragm or due to signal clipping by reaching a physical excursion limit, and such signal characteristics (when provided as the wind signal 110) may be detected by suitable signal analysis and/or processing. In yet other examples of a wind detector 126, power consumption by various components of an ANR system may be analyzed for indications of wind. For example, a windy environment may increase overall power consumption of an ANR system, such as by large signal amplitudes that may not be present in less windy environments. A measure of current provided to the ANR system, or of power provided more generally, may indicate the presence of wind. Additionally, a higher power consumption on one side (e.g., left or right) of a headphone system with ANR may indicate wind on the respective side, and detection of the power consumption discrepancy may be used as a wind detector 126.

Figure 4:
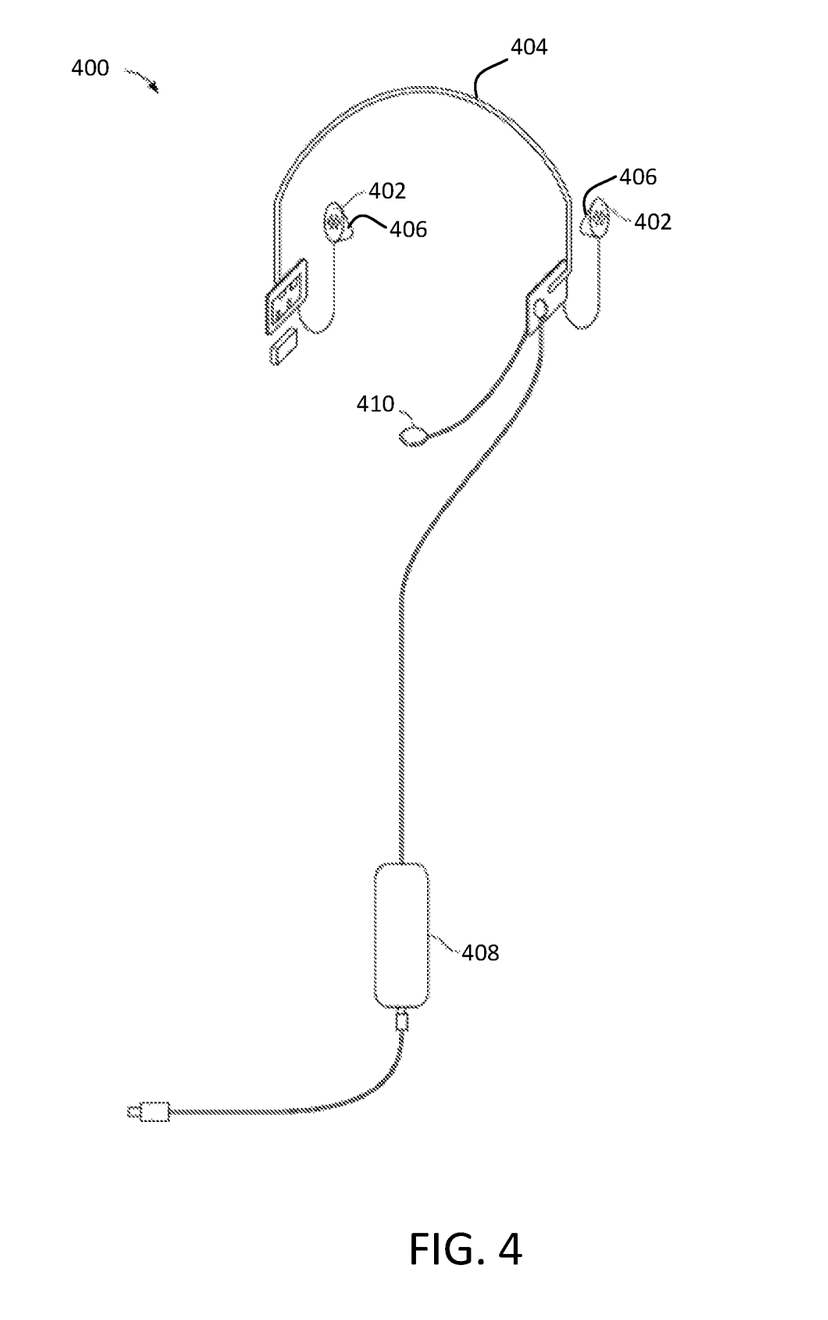
FIG. 4 is an in-ear headphone structure according to various examples discussed herein.

According to various examples, each of the headphone system 100 of FIG. 1 and the headphone system 200 of FIG. 2 has a variety of possible implementations. One example implementation may include an in-ear headphone structure, such as the in-ear structure illustrated in FIG. 4. In particular, FIG. 4 illustrates an external view of an in-ear headphone system 400. In FIG. 4 the headphone system 400 includes earpieces 402 connected by a headband 404. Each earpiece 402 includes an ear cushion 406 and a speaker. Each ear cushion 406 defines an interior volume of the respective earpiece 402. In various examples, each ear cushion 406 substantially seals the ear canal of the listener from external noise to provide passive noise reduction (PNR) to the listener. The ear cushions 406 may include a conformable frusto-conically shaped structure that deflects inwardly when the earpiece 402 is urged into the ear canal of the listener. The frusto-conically shaped structure conforms to the features of the external ear at the transition region between the bowl of the concha and the ear canal.

It is appreciated that the headphone system 400 may further include a control circuit 408, one or more feedback microphones or feed-forward microphones (not shown), and a boom microphone 410. The feed-forward microphone may be disposed on an external portion of the earpiece 402 to detect external noise, and the feedback microphone may be disposed in the interior volume of the earpiece 402 proximate the speaker. It is appreciated that other arrangements of the feed-forward microphone, the feedback microphone, and the speaker may be employed based on the particular application. In addition, the shape and size of the earpiece 402 may be altered based on the desired design.

The construction of the headphone system 400 may be altered based on the particular implementation. For example, the headphone system 400 may be constructed as a mono headset and employ only one earpiece 402. Further, the headphone system 400 may include a headband that attaches behind a head of a wearer, or may omit the headband 404 altogether. Accordingly, the headphone system 400 is not limited to any particular implementation.

Figure 5:
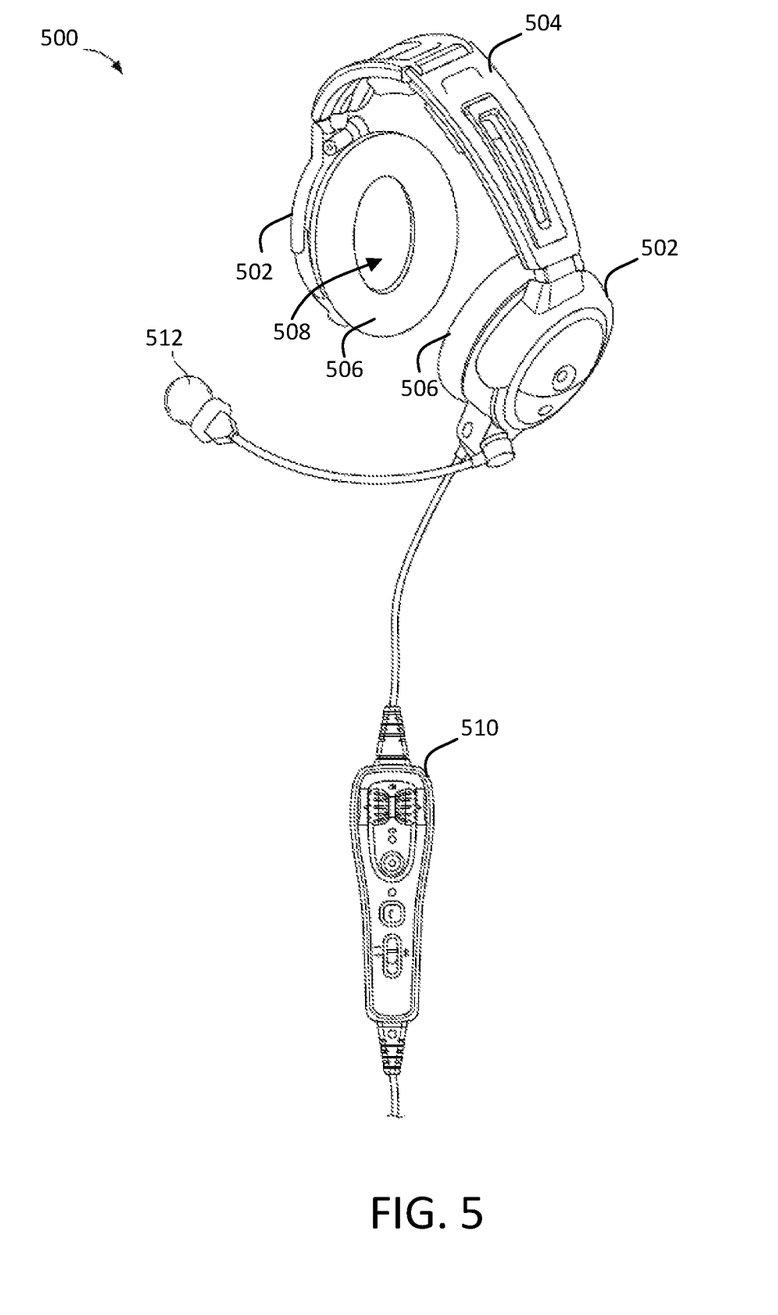
FIG. 5 is an over-the-ear headphone structure according to various examples discussed herein.

In certain other examples, the headphone system 100 or the headphone system 200 may be constructed to include an over-the-ear or an around-the-ear headphone structure. FIG. 5 illustrates one example of an around-the-ear type headphone system 500. In FIG. 5 the headphone system 500 includes earpieces 502 connected by a headband 504. Each earpiece 502 includes an ear cushion 506 and a speaker. Each ear cushion 506 defines an interior volume 508 of the respective earpiece 502. It is appreciated that the headphone system 500 may further include a control circuit 510, one or more feedback microphones or feed-forward microphones (not shown), and a boom microphone 512. The feed-forward microphone may be disposed on an external portion of the earpiece 502 to detect external noise, and the feedback microphone may be disposed in the interior volume 508 of the earpiece 502 proximate the speaker. It is appreciated that other arrangements of the feed-forward microphone, the feedback microphone, and the speaker may be employed based on the particular application. In addition, the shape and size of the earpiece 502 may be altered based on the desired design. For example, a smaller earpiece 502 may be employed in on-ear headset implementations as opposed to around-the-ear headset implementations.

The construction of the headphone system 500 may be altered based on the particular implementation. For example, the headphone system 500 may be constructed as a mono headset and employ only one earpiece 502 attached to the headband 504. The control circuit 510 is illustrated as including a user interface that allows the control circuit 510 to communicate with an external entity, such as a user. Examples of the components that may be employed within the user interface include buttons, switches, light-emitting diodes, touch screens, and displays, to name a few examples. Accordingly, the headphone system 500 is not limited to any particular implementation.

Figure 6:
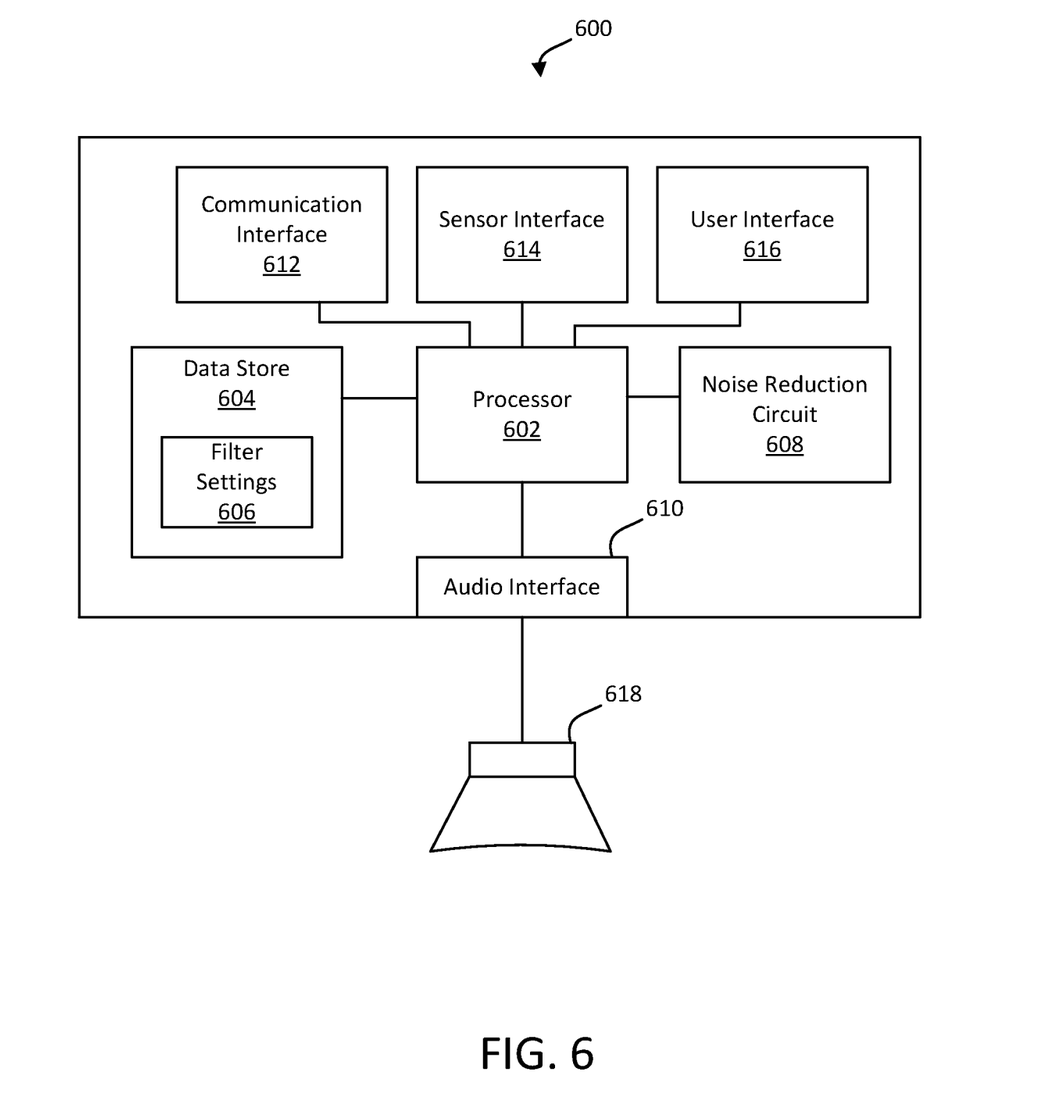
FIG. 6 is a block diagram of a control circuit according to various examples discussed herein.

As discussed above with reference to FIG. 1 and FIG. 2, in various examples the headphone system 100 and the headphone system 200 each include a control circuit 118 in communication with at least one speaker 102. FIG. 6 illustrates an example of a control circuit 600 that may be included within the headphone system 100 of FIG. 1 and/or the headphone system 200 of FIG. 2. The control circuit 600 may include a processor 602, a data store 604 (including filter settings 606 and/or transfer functions, among other information), a noise reduction circuit 608 (also referred to herein as "ANR circuitry"), an audio interface 610, a communication interface 612, a sensor interface 614, and a user interface 616. While not explicitly illustrated in FIG. 6, in certain examples the control circuit 600 may be coupled to a power source, such as a rechargeable battery, and/or a receptacle configured to receive one or more replaceable power sources (e.g., disposable batteries). The power source delivers power to the one or more components of the control circuit 600, as well as other components of the corresponding headphone system.

In FIG. 6, the processor 602 is coupled to the data store 604, the noise reduction circuit 608, and the various interfaces. The processor 602 executes a series of instructions that retrieves data (e.g., the filter settings 606) from the data storage 604. The data storage 604 may include a computer readable and writeable nonvolatile data storage medium configured to store non-transitory instructions and data. The medium may, for example, be optical disk, magnetic disk or flash memory, among others, and may be permanently affixed to, or removable from, the headphone structures shown in FIG. 1 and FIG. 2.

According to certain examples, the noise reduction circuit 608 is configured to perform the various acts and processes discussed herein to actively cancel external noise and/or residual noise. In particular, the noise reduction circuit 608 may apply a feedback filter to provide a feedback compensating signal and apply a feed-forward filter to provide a feed-forward compensating signal. The feedback compensating signal and the feed-forward compensating signal may be combined with an input audio signal to generate a noise-corrected driver signal that is delivered to a speaker 618 to provide acoustic energy to a listener. The noise reduction circuit 608 may be implemented using hardware, software, or a combination of hardware and software. For example, in one instance, the noise reduction circuit 608 is implemented as a software component that is stored in the data store and executed by the processor 602. However, in other examples the noise reduction circuit 608 may be an application-specific integrated circuit (ASIC) that is coupled to the processor 602. Accordingly, the noise reduction circuit 608 is not limited to one particular hardware and/or software implementation.

As discussed with reference to at least FIG. 2, in various examples the filter settings 606 include one or more sets of settings for the noise reduction circuit 608, and in particular, the feedback filter and/or the feed-forward filter. Each set of filter settings 606 includes instructions for the control circuit 600 to optimize ANR performance for a given wind condition. Each set of filter settings 606 may include an identifier that the control circuit 600 may reference to select the particular set of filter settings 606. Additionally, the filter settings 606 may be indexed by the identifier in a look-up table, or other suitable indexing structure.

In various examples, the control circuit 600 includes several interface components, such as the audio interface 610, the communication interface 612, the sensor interface 614, and the user interface 616 illustrated in FIG. 6. Each of the interface components is configured to exchange, e.g., send or receive, data with other components of a headphone system, or other devices in communication with the headphone system. In certain examples, the components may include buttons, switches, LEDs, microphones, speakers, and/or antennas, to name a few. According to various examples, the interface components may include hardware components, software components, or a combination of hardware and software components.

In certain examples, the audio interface 610 is coupled to one or more acoustic transducers, such as the illustrated speaker 618. The control circuit 600 (e.g., the noise reduction circuit 608) generates a driver signal based on a received input audio signal and the feedback compensating signal and/or feed-forward compensating signal. The driver signal is provided to the speaker 618 via the audio interface 610. While not illustrated in FIG. 6, the control circuit 600 may further include audio signal processing circuitry such as volume control circuitry, dynamic equalization circuitry, or other audio circuitry. Such circuitry may receive and process the input audio signal before providing the driver signal to the speaker 618 through the audio interface 610. In some instances the functionality of the audio signal processing circuitry may be incorporated within the audio interface 610.

In various examples, the components of the communication interface 612 couple the processor 602 to other devices, such as an audio signal source or an on-board aircraft system. In certain instances, the communication interface 612 allows the processor 602 to receive an audio signal from the audio signal source, which may include for example, a cellular phone, a portable media player, a computer-enabled watch, a personal computer, and/or one or more components of an on-board aircraft system, such as a pilot's radio and/or navigation system. The communication interface 612 may support any of a variety of standards and protocols including, for example, BLUETOOTH® and/or IEEE 802.11. The processor 602 may further perform one or more pairing processes to, for example, initially establish a communication link between the communication interface 612 and the other devices.

The user interface 616 shown in FIG. 6 may include a combination of hardware and/or software components that allow a corresponding headphone system in which the control circuit 600 is incorporated to communicate with an external entity, such as a user. These components may be configured to receive information from actions such as physical movement and/or verbal intonation. Examples of the components that may be employed within the user interface 616 include buttons, switches, light-emitting diodes, touch screens, displays, stored audio signals, voice recognition, or an application on a computer-enabled device in communication with the control circuit 600.

Thus, the various system interfaces allow the control circuit 600 to interoperate with a wide variety of devices in various contexts. It is appreciated that various interfaces may be removed from the control circuit 600 based on the particular construction and features of the headphone system. In addition, particular components may be adjusted or added to suit the particular construction of headphone system.

Various aspects and examples discussed herein are directed to a headphone system that includes one or more sensors to monitor wind conditions. Signals received are used to determine whether wind may interfere with the operation of active noise reduction components and appropriate settings for the active noise reduction circuit of the headphone system may be adjusted. For example, the headphone system may select one or more ANR filter settings for the headphone system to accommodate one or more influences of wind conditions in which the headphone system operates. Various aspects and examples provide improved noise cancellation functionality in a way that is not currently available in ANR headphone systems. While described herein primarily within the context of a headphone system, aspects and features described herein may be incorporated within other audio systems.

Having described above several aspects of at least one implementation, it is to be appreciated various alterations, modifications, and improvements will readily occur to those skilled in the art. Such alterations, modifications, and improvements are intended to be part of this disclosure and are intended to be within the scope of the description. Accordingly, the foregoing description and drawings are by way of example only, and the scope of the disclosure should be determined from proper construction of the appended claims, and their equivalents.

What is claimed is:

1. A headphone system comprising:
   an earpiece configured to define an acoustic volume;
   a speaker to provide acoustic energy to the acoustic volume based on a received driver signal;
   a feed-forward microphone acoustically coupled to an external environment to detect at least external noise and generate a feed-forward audio signal;
   a feedback microphone to detect at least residual noise within the acoustic volume, and generate a feedback audio signal; and
   a control circuit including an interface to receive a wind signal and configured to detect wind based at least in part upon the wind signal, the control circuit also configured to adjust the feed-forward audio signal based on the wind detection, and to adjust the feedback audio signal by adjusting one or more feedback filter coefficients applied to the feedback audio signal based on the wind detection,
   wherein the control circuit is configured to detect the wind by at least one of the wind signal being provided by a user indication, the wind signal indicating an equipment setting, detecting a direct current component in the wind signal, detecting a non-linear component in the wind signal, and detecting a whistle component in the wind signal.

2. The headphone system of claim 1, wherein the control circuit is configured to adjust the feed-forward audio signal by adjusting one or more feed-forward filter coefficients applied to the feed-forward audio signal based on the wind detection.

3. The headphone system of claim 2, further comprising a data store comprising a plurality of feed-forward filter coefficient sets, the control circuit being configured to select a first feed-forward filter coefficient set from among the plurality of feed-forward filter coefficient sets based on the wind detection.

4. The headphone system of claim 1, wherein the interface is configured to receive the feed-forward audio signal as the wind signal, and the control circuit is configured to detect wind based at least in part on the feed-forward audio signal.

5. The headphone system of claim 4, wherein the control circuit is further configured to analyze a spectral content of the feed-forward audio signal and to detect wind based at least in part on the spectral content.

6. The headphone system of claim 4, wherein the feed-forward microphone is a first feed-forward microphone to generate a first feed-forward audio signal and the headphone system further comprises a second feed-forward microphone to generate a second feed-forward audio signal, and the control circuit is configured to detect wind based at least in part on a comparison of the first feed-forward audio signal and the second feed-forward audio signal.

7. The headphone system of claim 1, further comprising a data store comprising a plurality of feedback filter coefficient sets, the control circuit being configured to select a first feedback filter coefficient set from among the plurality of feedback filter coefficient sets based on the wind detection.

8. The headphone system of claim 1, wherein the control circuit is further configured to detect a plurality of wind levels based at least upon the wind signal, and to adjust the feed-forward audio signal based at least in part on the detected wind level.

9. The headphone system of claim 1, wherein the control circuit is configured to adjust the feed-forward audio signal by disabling the feed-forward audio signal.

10. The headphone system of claim 9, wherein the control circuit is configured to disable the feed-forward audio signal by removing a microphone bias signal from the feed-forward microphone.

11. The headphone system of claim 9, wherein the control circuit is configured to disable the feed-forward audio signal by applying a filter of zero gain to the feed-forward audio signal.

12. A headphone system comprising:
    an earpiece configured to define an acoustic volume;
    a speaker to provide acoustic energy to the acoustic volume based on a received driver signal;
    a feedback microphone to detect at least residual noise within the acoustic volume and generate a feedback audio signal;
    a feed-forward microphone to detect at least external noise and generate a feed-forward audio signal; and
    a control circuit including an interface to receive the feed-forward audio signal and configured to detect the presence of wind, and to distinguish between a plurality of levels of detected wind, to adjust a transfer function of a feedback filter applied to the feedback audio signal based on the wind detection, and to adjust the feed-forward audio signal based on the wind detection.

13. The headphone system of claim 12, wherein the control circuit is configured to adjust a transfer function of a feed-forward filter applied to the feed-forward audio signal based on the wind detection.

14. The headphone system of claim 13, further comprising a data store comprising a plurality of feed-forward filter coefficient sets, the control circuit being configured to select a first feed-forward filter coefficient set from among the plurality of feed-forward filter coefficient sets based on the wind detection.

15. The headphone system of claim 12, further comprising a data store comprising a plurality of feedback filter coefficient sets, the control circuit being configured to select a first feedback filter coefficient set from among the plurality of feedback filter coefficient sets based on the wind detection.

16. The headphone system of claim 12, wherein the feed-forward microphone is a first feed-forward microphone to generate a first feed-forward audio signal and the headphone system further comprises a second feed-forward microphone to generate a second feed-forward audio signal, and the control circuit is configured to detect wind based at least in part on a comparison of the first feed-forward audio signal and the second feed-forward audio signal.

17. A method for operating a headphone system comprising:

providing acoustic energy from a speaker of a headphone system to an acoustic volume based on a driver signal received at the speaker;

detecting noise external to the acoustic volume using a feed-forward microphone;

detecting wind by analyzing the noise external to the acoustic volume;

generating a feed-forward audio signal at least partially indicative of the noise;

adjusting the feed-forward audio signal based at least in part on the wind detection, detecting residual noise within the acoustic volume;

generating a feedback audio signal at least partially indicative of the residual noise; and filtering the feedback audio signal by a feedback filter having a filter coefficient set selected from among a plurality of stored filter coefficient sets based at least in part on the wind detection.

18. The method of claim 17, wherein adjusting the feed-forward audio signal based on the wind detection comprises adjusting a transfer function of a feed-forward filter applied to the feed-forward audio signal based on the wind detection.

19. The method of claim 18, wherein adjusting the transfer function of the feed-forward filter includes selecting a filter coefficient set from among a plurality of filter coefficient sets based on the wind detection, and applying the selected filter coefficient set to the feed-forward filter.

20. The method of claim 17, wherein adjusting the feed-forward audio signal comprises disabling the feed-forward audio signal.

21. The method of claim 20, wherein disabling the feed-forward audio signal comprises removing a microphone bias signal from the feed-forward microphone.

22. The method of claim 20, wherein disabling the feed-forward audio signal comprises applying a filter of zero gain to the feed-forward audio signal.

* * * * *